(12) United States Patent
Cook et al.

(10) Patent No.: US 6,735,980 B2
(45) Date of Patent: May 18, 2004

(54) RECOVERY OF KRYPTON AND XENON

(75) Inventors: Stephen John Cook, Macungie, PA (US); John Louis Griffiths, Pittsburgh, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 332 days.

(21) Appl. No.: 10/039,866

(22) Filed: Jan. 4, 2002

(65) Prior Publication Data

US 2003/0129127 A1 Jul. 10, 2003

(51) Int. Cl.$^7$ .............. F25J 3/04; F25J 3/08; C01B 23/00
(52) U.S. Cl. .......... 62/640; 62/925; 252/372; 423/210
(58) Field of Search ............ 62/640, 925; 252/372; 423/210

(56) References Cited

U.S. PATENT DOCUMENTS

| | | | |
|---|---|---|---|
| 2,482,304 A | 9/1949 | Van Nuys | 62/175.5 |
| 3,037,359 A | 6/1962 | Knapp | 62/22 |
| 3,274,750 A | 9/1966 | Ross | 55/16 |
| 4,115,081 A | 9/1978 | Ohno et al. | 55/64 |
| 4,401,448 A * | 8/1983 | La Clair | 62/648 |
| 4,687,498 A | 8/1987 | Maclean et al. | 62/17 |
| 4,752,311 A | 6/1988 | MacLean et al. | 62/18 |
| 4,782,096 A | 11/1988 | Banquy | 518/704 |
| 5,100,447 A | 3/1992 | Krishnamurthy et al. | 62/22 |
| 5,122,173 A | 6/1992 | Agrawal et al. | 62/22 |
| 5,218,003 A | 6/1993 | Lewnard et al. | 518/700 |
| 5,313,802 A * | 5/1994 | Agrawal et al. | 62/648 |
| 5,547,492 A | 8/1996 | Cho et al. | 95/100 |
| 5,743,944 A | 4/1998 | Gross et al. | 96/181 |
| 6,164,089 A | 12/2000 | Sweeny et al. | 62/640 |
| 6,351,970 B1 * | 3/2002 | Hahn et al. | 62/648 |

FOREIGN PATENT DOCUMENTS

| | | | |
|---|---|---|---|
| FR | 1538659 | 9/1968 | |
| JP | 07270067 A | * 10/1995 | F25J/3/04 |

OTHER PUBLICATIONS

Senden, M.M.G., "The Shell Middle Distillate Synthesis Process: Commercial Plant Experience and Outlook into the Future", Shell International Oil Products B.V., *Petrole et Techniques*, vol. 415, 1998, pp 94–97.

(List continued on next page.)

*Primary Examiner*—Stanley S. Silverman
*Assistant Examiner*—Jonas N. Strickland
(74) *Attorney, Agent, or Firm*—Robert J. Wolff (57) ABSTRACT

A method for recovering krypton and xenon from air comprises (a) separating an air feed stream into oxygen-enriched and nitrogen-enriched product streams; (b) reacting the oxygen-rich product stream with a hydrocarbon feed in a synthesis gas generation process to yield a synthesis gas stream comprising hydrogen, carbon oxides, krypton, and xenon, which synthesis gas stream contains essentially no oxygen; (c) introducing the synthesis gas stream into a synthesis gas conversion process and converting the synthesis gas stream into a liquid synthesis product stream and an unreacted synthesis gas stream; (d) recycling at least a portion of the unreacted synthesis gas stream to the synthesis gas generation process; (e) reducing the pressure of the liquid synthesis product stream to yield a two-phase reduced-pressure product stream, and separating the two-phase reduced-pressure product stream into a final liquid synthesis product stream and a gas stream enriched in krypton and xenon; and (f) separating the gas stream enriched in krypton and xenon into a purge gas stream and a gas product stream further enriched in krypton and xenon.

24 Claims, 5 Drawing Sheets

OTHER PUBLICATIONS

"Process Makes Mid–Distillates from Natural Gas", Oil & Gas Journal, Feb. 17, 1986, Technology pp 74–75.

"Fuels, Synthetic, Liquid Fuels", Section 2, Indirect Liquefaction/Conversion to Liquid Fuels, *Kirk–Othmer Encyclopedia of Chemical Technology*, Copyright 1994 by John Wiley & Sons, Inc., Posted online Dec. 4, 2000.

"Methanol", Section 4, Manufacturing and Processing, *Kirk–Othmer Encyclopedia of Chemical Technology*, John Wiley & Sons, Inc., Posted online Dec. 4, 2000.

Helium Group Gases, Section 4, Production, *Kirk–Othmer Encyclopedia of Chemical Technology*, John Wiley & Sons, Inc., Posted online Dec. 4, 2000.

Arutyunov et al., "Recovery of Krypton and Xenon from Blow–Off Gases from Ammonia Synthesis", Khim. Prom–st. (Moscow), (1), 35–37 (1991).

* cited by examiner

RECOVERY OF KRYPTON AND XENON

BACKGROUND OF THE INVENTION

Air contains small concentrations of the valuable inert gases helium, neon, argon, krypton, and xenon. Neon, argon, krypton, and xenon historically have been recovered as secondary products in the cryogenic separation of air into oxygen and/or nitrogen products. Argon, krypton, and xenon also can be recovered from the purge gas generated in the production of ammonia from synthesis gas generated from air and natural gas. Krypton and xenon are useful in a number of specialized fields including research, medicine, instrumentation, lighting, and space applications, and demand is expected to increase as these applications expand.

Because air contains only 1.14 and 0.087 ppmv of krypton and xenon, respectively, recovery of these components by the cryogenic separation of air is technically complex and costly. Recovery is complicated further by the presence of light hydrocarbons, particularly methane, in the air feed to air separation plants. Krypton, xenon, and methane, by virtue of their boiling points relative to oxygen and nitrogen, are concentrated in the liquid oxygen during the distillation process. In the separation of krypton and xenon from the liquid oxygen, the formation of flammable mixtures of methane and oxygen potentially can occur. Numerous processes have been developed in the air separation industry to circumvent this problem, but the processes are complex and safety is an ongoing concern in plant operation. Methods to recover krypton and xenon from air without the potential for forming flammable hydrocarbon-oxygen mixtures are therefore highly desirable.

The invention described below and defined by the claims which follow offers a method for recovering krypton and xenon from air without the potential to form such flammable hydrocarbon-oxygen mixtures in the krypton-xenon separation process. The method can be integrated with processes for the production and conversion of synthesis gas into liquid synthesis products wherein the synthesis gas is produced by partial oxidation of hydrocarbons with oxygen.

BRIEF SUMMARY OF THE INVENTION

The invention relates to a method for recovering krypton and xenon from air which comprises:

(a) separating an air feed stream into oxygen-enriched and nitrogen-enriched product streams;

(b) reacting the oxygen-rich product stream with a hydrocarbon feed in a synthesis gas generation process to yield a synthesis gas stream comprising hydrogen, carbon oxides, krypton, and xenon, which synthesis gas stream contains essentially no oxygen;

(c) introducing the synthesis gas stream into a synthesis gas conversion process and converting the synthesis gas stream into a liquid synthesis product stream and an unreacted synthesis gas stream;

(d) recycling a portion of the unreacted synthesis gas stream to the synthesis gas conversion process; and (e) separating another portion of the unreacted synthesis gas stream into a purge gas stream and a gas product stream enriched in krypton and xenon.

The hydrocarbon feed may be natural gas. The liquid synthesis product may comprise methanol or paraffinic hydrocarbons. The method may further comprise introducing steam into the synthesis gas generation process.

The separating of the remaining portion of the unreacted synthesis gas stream into the purge gas stream and the gas product stream enriched in krypton and xenon may be effected by one or more process steps selected from the group consisting of catalytic combustion, amine-based absorption, condensation and phase separation, pressure swing adsorption, temperature swing adsorption, and cryogenic distillation.

The method may further comprise reducing the pressure of the liquid product stream to yield a two-phase reduced-pressure product stream, and separating the two-phase reduced-pressure product stream into a final liquid synthesis product stream and a gas stream enriched in krypton and xenon. The method also may further comprise combining the gas stream enriched in krypton and xenon with another portion of the unreacted synthesis gas stream.

The purge gas stream may comprise at least hydrogen, carbon monoxide, and methane, and optionally a portion of the purge gas stream may be recycled to the synthesis gas generation process. Optionally a portion of the purge gas stream may be recycled to the synthesis gas conversion process. Another portion of the purge gas stream may be recycled to the synthesis gas generation process In another embodiment, the invention relates to a method for recovering krypton and xenon from air which comprises:

(a) separating an air feed stream into oxygen-enriched and nitrogen-enriched product streams in an air separation process;

(b) reacting the oxygen-rich product stream with a hydrocarbon feed in a synthesis gas generation process to yield a synthesis gas stream comprising hydrogen, carbon oxides, krypton, and xenon, which synthesis gas stream contains essentially no oxygen;

(c) introducing the synthesis gas stream into a synthesis gas conversion process and converting the synthesis gas stream into a liquid synthesis product stream and an unreacted synthesis gas stream;

(d) recycling at least a portion of the unreacted synthesis gas stream to the synthesis gas generation process;

(e) reducing the pressure of the liquid synthesis product stream to yield a two-phase reduced-pressure product stream, and separating the two-phase reduced-pressure product stream into a final liquid synthesis product stream and a gas stream enriched in krypton and xenon; and (f) separating the gas stream enriched in krypton and xenon into a purge gas stream and a gas product stream further enriched in krypton and xenon.

A portion of the unreacted synthesis gas stream may be combined with the gas stream enriched in krypton and xenon prior to (f). The hydrocarbon feed may be natural gas and the liquid synthesis product may comprise methanol. Alternatively, the liquid synthesis product may comprise paraffinic hydrocarbons. The method of may further comprise introducing steam into the synthesis gas generation process.

The separating of the remaining portion of the unreacted synthesis gas stream into the gas product stream enriched in krypton and xenon and the purge gas stream may be effected by one or more process steps selected from the group consisting of catalytic combustion, amine-based absorption, condensation and phase separation, pressure swing adsorption, temperature swing adsorption, and cryogenic distillation.

The purge gas stream may comprise at least hydrogen, carbon monoxide, methane, krypton, and xenon. A portion of the purge gas stream may be recycled to the synthesis gas generation process.

If desired, a portion of the purge gas stream may be recycled to the synthesis gas conversion process and optionally another portion of the purge gas stream may be recycled to the synthesis gas generation process. A portion of the purge gas stream may be recycled to the air separation process.

DETAILED DESCRIPTION OF THE INVENTION

The cryogenic separation of air yields an oxygen product which is enriched in krypton and xenon. Krypton and xenon are present in ambient air at 1.14 and 0.087 ppmv, respectively, and typically are concentrated in the oxygen product by a factor of at least four. In the present invention, oxygen from a cryogenic air separation unit is reacted with a hydrocarbon feedstock such as natural gas to yield a synthesis gas product containing hydrogen, carbon oxides (i.e. carbon monoxide and carbon dioxide), methane, water, and inert gases including krypton and xenon. This synthesis gas contains essentially no oxygen, which means that the concentration of oxygen is below about 0.1 vol %. The recovery of krypton and xenon from this synthesis gas as described below is carried out with a significantly reduced possibility of forming flammable mixtures of hydrocarbons and oxygen compared with recovery by cryogenic separation from air.

Figure 1:
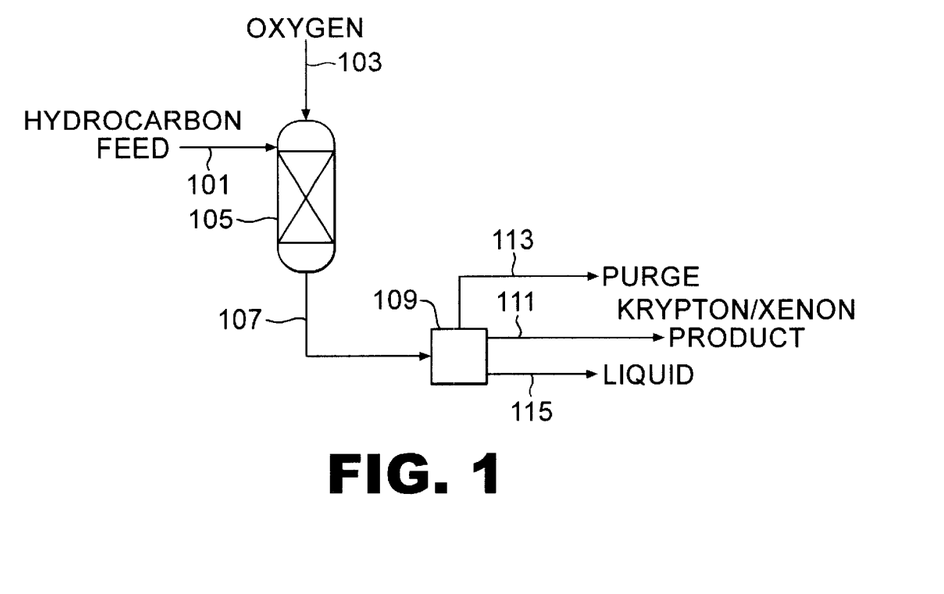
FIG. 1 is a simplified flow diagram illustrating the present invention.
Figure 2:
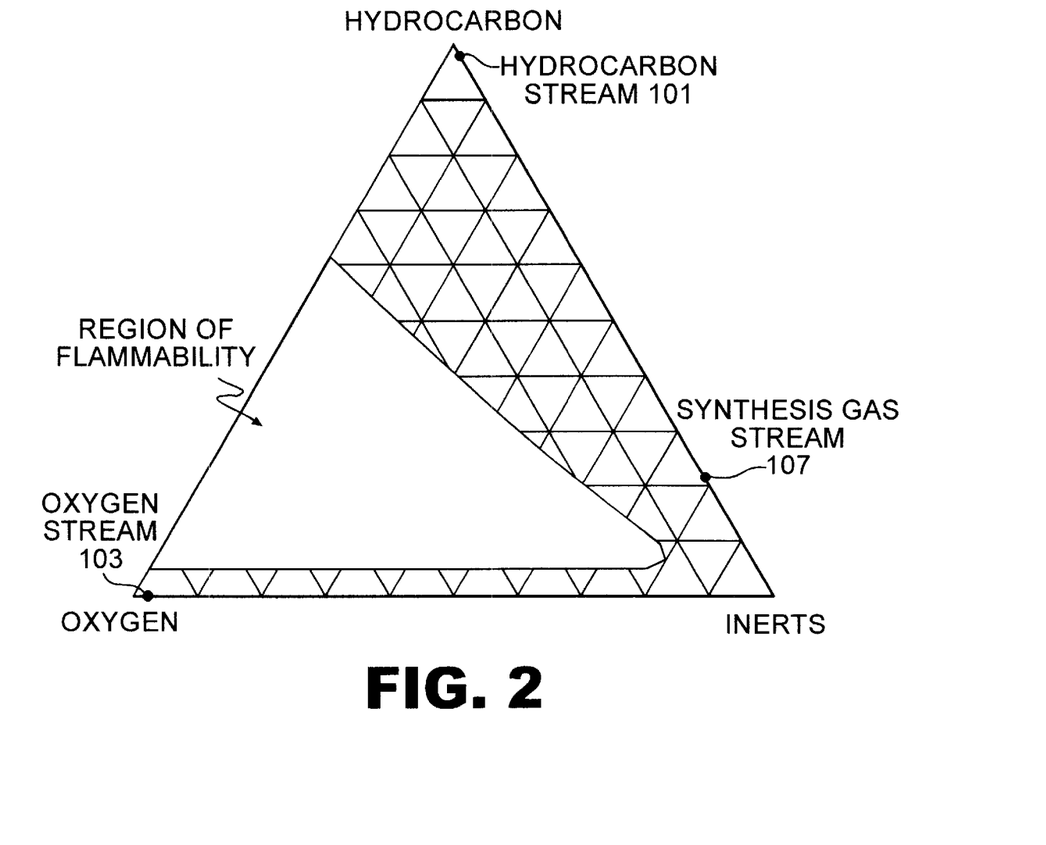
FIG. 2 is a flammability chart showing a typical region of flammability for mixtures of hydrocarbon, oxygen, and inerts.

A generalized schematic diagram of the invention is given in FIG. 1. Hydrocarbon stream 101 is reacted with oxygen-enriched stream 103 in reactor 105 to yield synthesis gas stream 107 which contains hydrogen, carbon monoxide, carbon dioxide, methane, water, and inert gases including krypton and xenon. This synthesis gas contains essentially no oxygen because hydrocarbon stream 101 is provided in excess of that required to consume the oxygen in oxygen-enriched stream 103. If any unconsumed oxygen is present in synthesis gas stream 107, it is at a concentration of less than 0.1 vol %. In converting hydrocarbon stream 101 and oxygen-enriched stream 103 into synthesis gas stream 107, no flammable oxygen-hydrocarbon streams are created. Typical concentration locations of hydrocarbon stream 101, oxygen-enriched stream 103, and synthesis gas stream 107 are shown in the ternary flammability chart of FIG. 2. Controlled oxidation reactions consume essentially all of the oxygen in reactor 105 and as a result no separate oxygen-hydrocarbon streams that could have compositions within the region of flammabiity in FIG. 2 are generated.

Referring again to FIG. 1, synthesis gas stream 107 is introduced into synthesis gas conversion and krypton-xenon recovery zone 109, wherein there is produced, as described in detail below, product gas stream 111 enriched krypton and xenon, waste or purge gas stream 113, and liquid hydrocarbon product stream 115. Hydrocarbon feed 101 may be any carbonaceous material which can be converted into synthesis gas by reaction with oxygen-enriched stream 103. For example, stream 101 could be natural gas, naphtha, heavy hydrocarbons, petroleum coke, or biomass. Alternatively, synthesis gas stream 107 can be generated by the gasification of coal. Oxygen-enriched stream 101 is defined as a stream which contains oxygen at a higher concentration than that of air. Typically, the oxygen concentration in the oxygen-enriched stream may be greater than 80 vol %, may range up to 95 vol %, and in some applications may be as high as 99.5 vol %.

Figure 3:
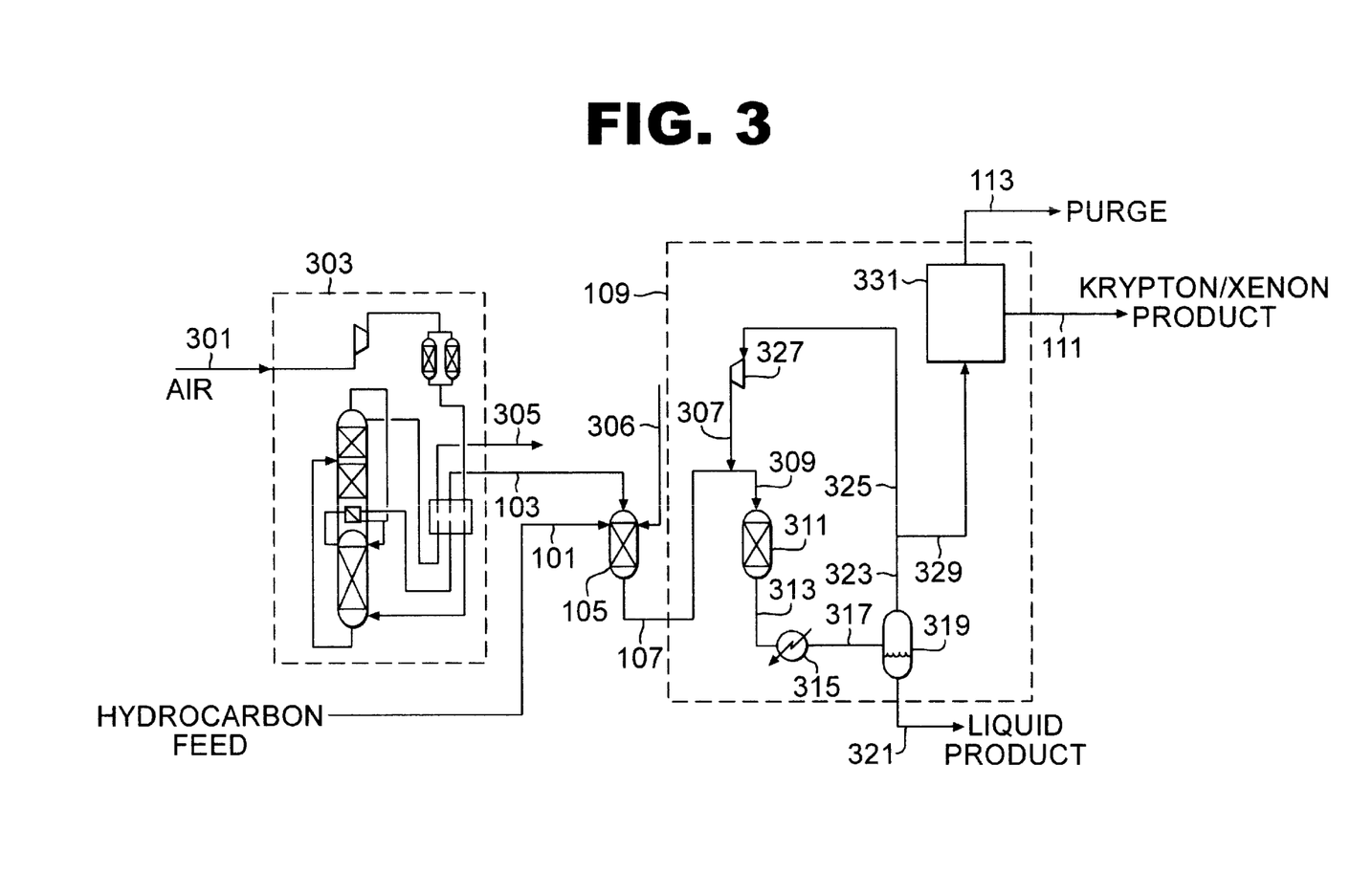
FIG. 3 is a schematic flow diagram of an exemplary embodiment of the present invention.

An exemplary embodiment of the invention is illustrated in FIG. 3. Atmospheric air 301 is separated in air separation unit 303 to yield at least oxygen-enriched product stream 103 and nitrogen-enriched product stream 305. Air separation unit 303 may use any of the numerous cryogenic air separation cycles known in the art. Oxygen-enriched product stream 103 has an oxygen concentration in the range recited above, and could be, for example, 99.5 vol % oxygen. Hydrocarbon feed stream 101, oxygen-enriched stream 103, and optionally steam stream 306 are reacted in synthesis gas generation system 105 to yield synthesis gas stream 107.

Synthesis gas generation system 105 may be a partial oxidation reactor system which can utilize any of the partial oxidation processes known in the art. These include, for example, the following processes: autothermal reforming of natural gas; partial oxidation of hydrocarbon liquids such as naphtha; combined reforming, which is steam-methane reforming followed by oxygen-blown partial oxidation; or gas-heated reforming, which is combined reforming in which heat is provided to the endothermic steam-methane reforming step by the exothermic oxygen-blown partial oxidation step. These known processes are described in *Methanol*, Section 4.2, Synthesis Gas Generation Routes, in the *Kirk-Othmer Encyclopedia of Chemical Technology*, John Wiley & Sons, 1995, posted online Dec. 4, 2000.

Synthesis gas stream 107, which contains hydrogen, carbon monoxide, carbon dioxide, methane, water, and inert gases including krypton and xenon, is combined with recycle gas stream 307 (later defined) and combined stream 309 is introduced into synthesis gas conversion system 311. In this reaction system the synthesis gas is partially converted into a hydrocarbon product which leaves the reaction system in admixture with unreacted synthesis gas as reactor effluent stream 313. This reactor effluent is cooled and partially condensed in heat exchanger 315 and the cooled two-phase stream is separated in separator 319 into liquid synthesis product stream 321 and unreacted synthesis gas stream 323.

Synthesis gas conversion system 311 may utilize any known process which converts synthesis gas into a liquid synthesis product. This synthesis product may be, for example, methanol, a mixture of paraffinic hydrocarbons, or a mixture of methanol and dimethyl ether. Methanol may be produced from synthesis gas stream 107 by known methanol synthesis processes, for example, as described in *Methanol*, Section 4, Manufacturing and Processing, in the *Kirk-Othmer Encyclopedia of Chemical Technology*, John Wiley & Sons, 1995, posted online Dec. 4, 2000. Paraffinic hydrocarbons may be produced by processes described in *Fuels, Synthetic, Liquid Fuels*, Section 2, Indirect Liquefaction/Conversion to Liquid Fuels, in the *Kirk-Othmer Encyclopedia of Chemical Technology*, John Wiley & Sons, 1995, posted online Dec. 4, 2000. Mixtures of dimethyl ether and methanol may be produced, for example, according to the process described in U.S. Pat. No. 5,218,003.

In the embodiment of FIG. 3, unreacted synthesis gas stream 323 is divided into recycle stream 325 and purge stream 329. Recycle stream 325 is compressed in compressor 327, and compressed unreacted synthesis gas stream 307 is combined with synthesis gas stream 107 as earlier described. By virtue of this recycle step, krypton and xenon become increasingly concentrated in the synthesis loop and in unreacted synthesis gas 323. Purge stream 329 contains concentrations of krypton and xenon which may be 7 to 20 times higher than the respective concentrations in ambient air. This purge stream also contains, as shown in the Example below, significant concentrations of hydrogen, carbon monoxide, carbon dioxide, and methane. The purge stream also contains minor concentrations of nitrogen, argon, methanol, and water.

Purge stream 329 may be processed in krypton/xenon recovery system 331 to concentrate the krypton and xenon further for final separation using any combination of known gas separation steps. In one embodiment, for example, carbon dioxide may be removed from purge stream 329 by an amine-based absorption process using monodiethanol amine (MDEA), the carbon dioxide-free purge gas may be cooled to condense and remove water and methanol, and the residual water and methanol in the purge gas may be removed by pressure or temperature swing adsorption. The remaining gas, which contains major concentrations of hydrogen, carbon monoxide, and methane with minor concentrations of nitrogen, argon, krypton, and xenon, may be further separated by cryogenic distillation to yield enriched krypton/xenon product gas stream 111 and waste or purge stream 113.

In an alternative embodiment, purge stream 329 may be reacted catalytically with stoichiometric amounts of oxygen from oxygen-enriched stream 103 to convert the hydrogen, carbon monoxide, methane, and methanol to carbon dioxide and water, and then using the additional separation steps outlined in the above embodiment. In this alternative embodiment, the final distillation step would be simpler than that of the above embodiment, since the final gas stream to be separated would be at a much lower flow rate and would contain only nitrogen, argon, krypton, and xenon. Typical krypton and xenon recoveries from air feed stream 301 using either embodiment may range from 50 to 95%.

Figure 4:
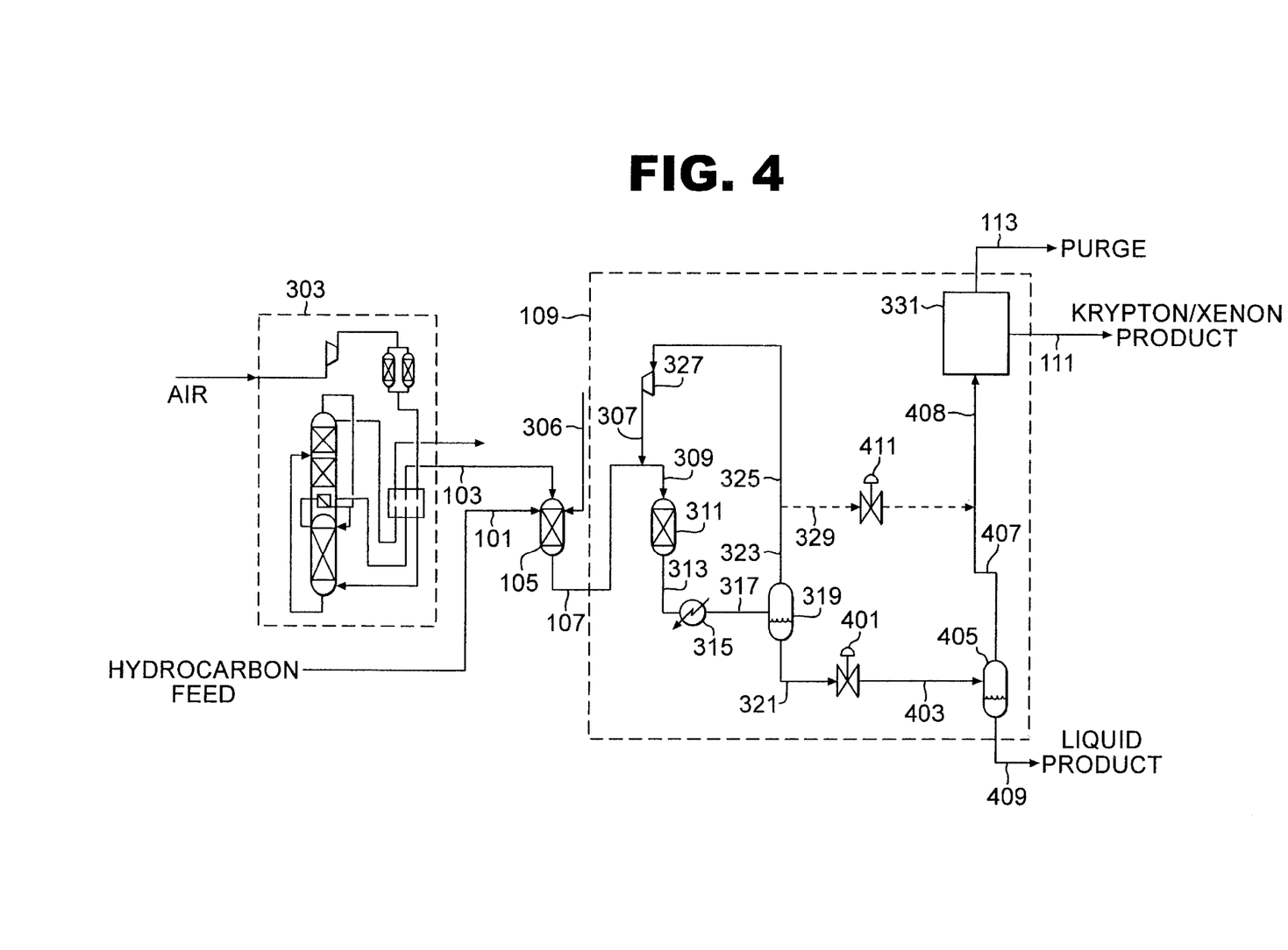
FIG. 4 is a schematic flow diagram of another exemplary embodiment of the present invention.

An alternative exemplary embodiment is illustrated in FIG. 4. In this alternative, liquid synthesis product stream 321 is reduced in pressure across valve 401 to release dissolved gas (including krypton and xenon) and reduced-pressure two-phase stream 403 is separated in separator 405. Final liquid synthesis product stream 409 and released gas stream 407 are withdrawn therefrom, and released gas stream 407 is processed in krypton/xenon recovery system 331. Optionally, a portion 329 of unreacted synthesis gas stream 323 may be reduced in pressure across valve 411 and combined with released gas stream 407. The combined stream then may be processed as described above in krypton/xenon recovery system 331.

Figure 5:
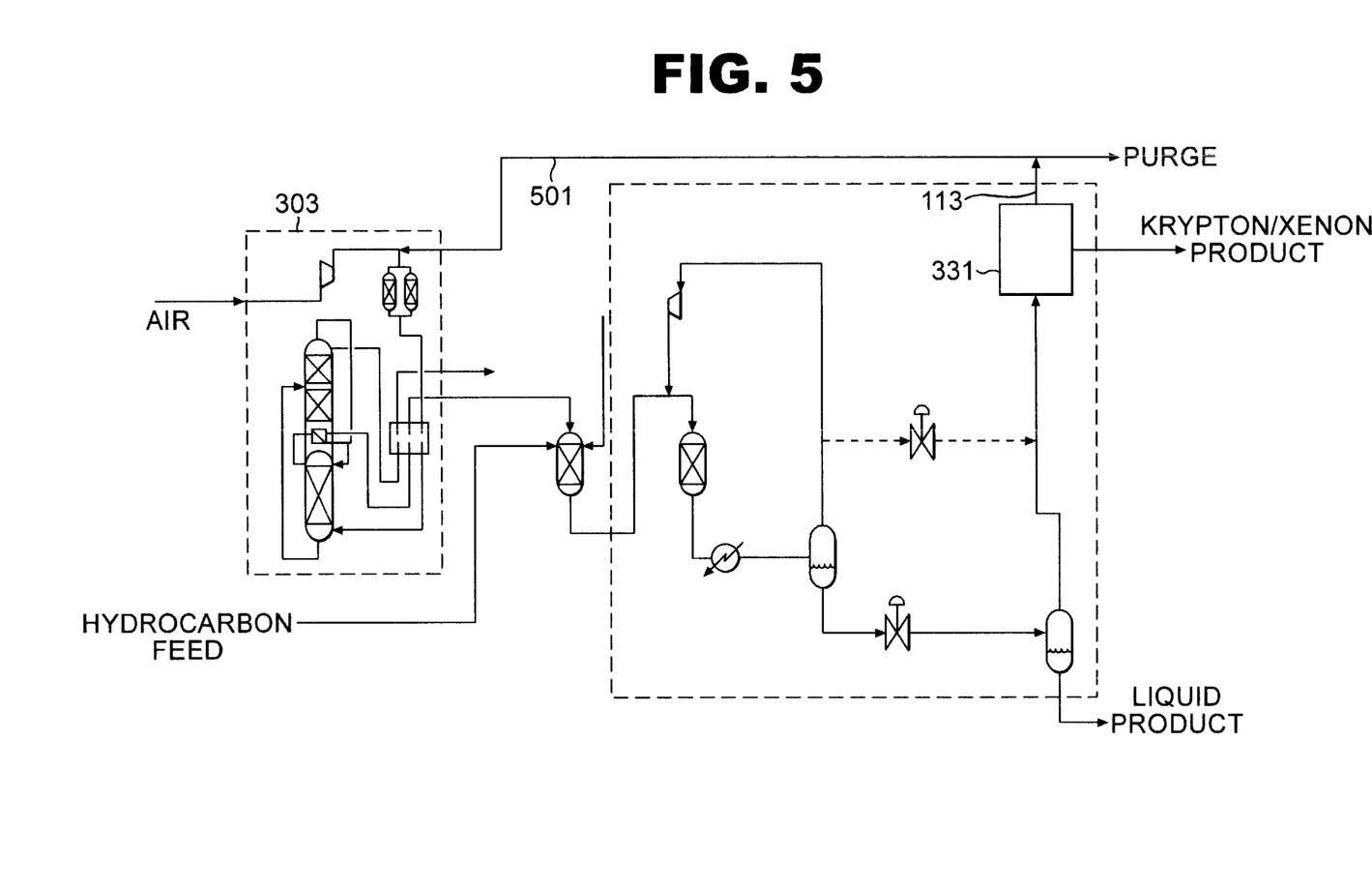
FIG. 5 is a schematic flow diagram of an alternative exemplary embodiment of the present invention.
Figure 6:
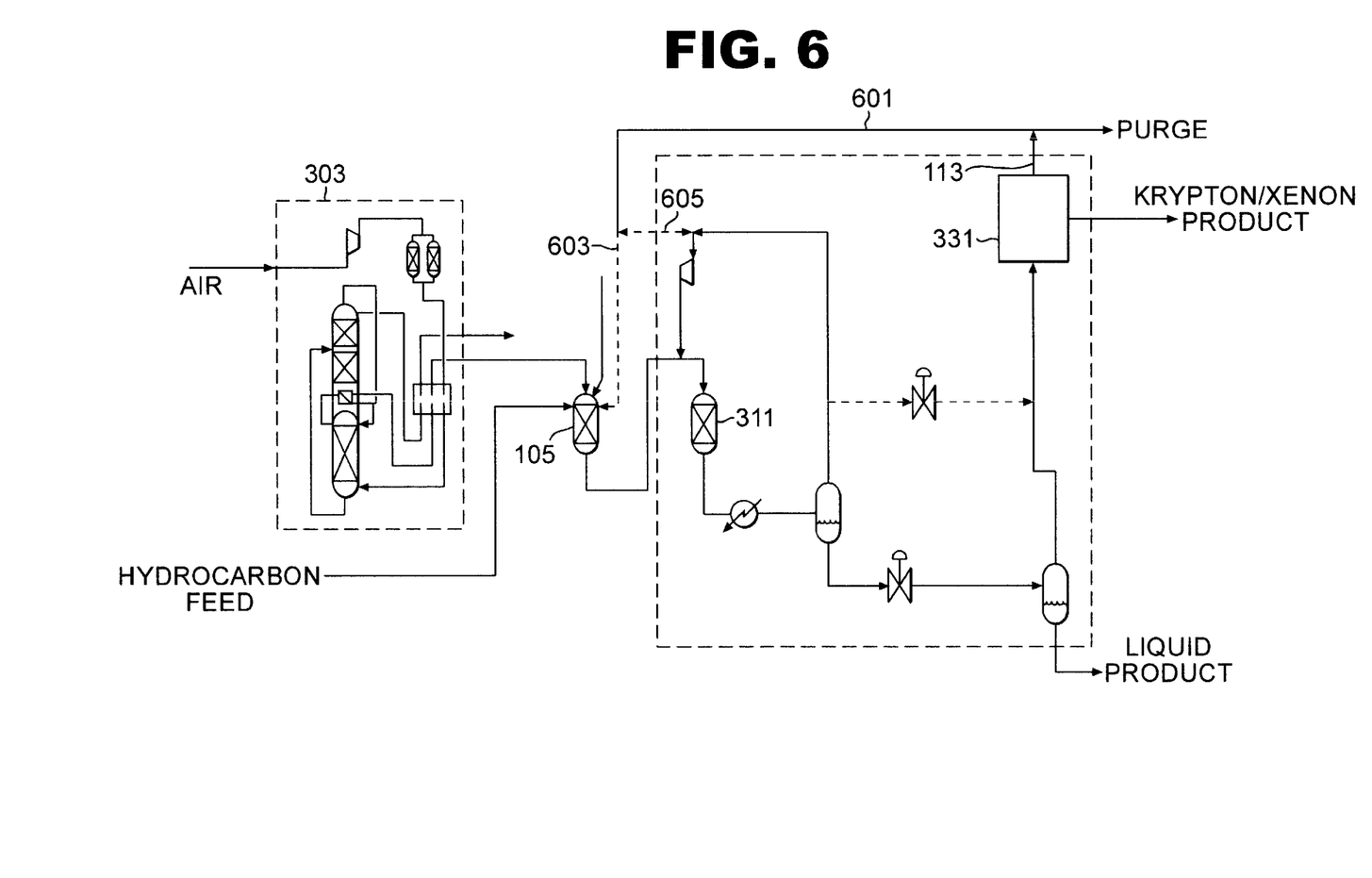
FIG. 6 is a schematic flow diagram of another alternative exemplary embodiment of the present invention.

An optional embodiment is illustrated in FIG. 5 in which a portion of purge gas 113 from krypton/xenon recovery system 331 is recycled as stream 501 to air separation unit 303 to increase krypton and xenon recovery. Since stream 501 may contain residual hydrocarbons, it is likely that a hydrocarbon removal step (not shown) would be needed prior to air separation unit 303. Another optional embodiment is shown in FIG. 6. In this option, a portion of purge gas 113 from krypton/xenon recovery system 331 may be recycled via stream 601 to either synthesis gas generation system 105 as stream 603 or synthesis gas conversion system 311 as stream 605. Alternatively, a portion of purge gas 113 can be recycled to both synthesis gas generation system 105 as stream 603 and synthesis gas conversion system 311 as stream 605.

EXAMPLE

The invention is illustrated but not limited by the following Example. The embodiment of FIG. 4 was simulated by a heat and material balance to illustrate the invention. In this embodiment, oxygen stream 103 is provided by air separation unit and contains 99.51 vol % oxygen. This oxygen is reacted with natural gas stream 101 and steam 306 in partial oxidation reactor system 105 to yield synthesis gas stream 107 which has a hydrogen to carbon monoxide molar ratio of about 2. This synthesis gas is combined with recycle stream 307 and partially converted to methanol in methanol reaction system 311. This reaction yields reactor product stream 313, which is cooled and separated in separator 319 to yield methanol-rich pressurized liquid stream 321 and unreacted synthesis gas 323.

Methanol-rich pressurized liquid stream 321 is reduced in pressure across valve 401 and the resulting two-phase stream 403 is separated into methanol liquid product stream 409 and gas stream 407 enriched in krypton and xenon. A portion of unreacted synthesis gas stream 323 is withdrawn as stream 329, which is reduced in pressure across valve 411. The reduced pressure gas is combined with gas stream 407 and the resulting combined stream 408 enriched in krypton and xenon is introduced into krypton and xenon recovery system 331. The remaining portion of unreacted synthesis gas stream 323 is recycled as stream 325 to compressor 327 and stream 309 is returned to methanol reaction system 311.

Stream 408 enriched in krypton and xenon is further enriched in krypton and xenon recovery system 331 by the alternative embodiment described earlier. Final enriched product stream 111 is withdrawn and contains 73.9 vol % krypton and 6.33 vol % xenon. Individual krypton and xenon products may be recovered by a final cryogenic distillation step.

A stream summary of the heat and material balances for this Example is given in Table 1 below. It is seen that 64.9% of the krypton and 78.9% of the xenon in the feed air stream 301 are recovered in product stream 111.

TABLE 1

Stream Summary for Example
(Concentrations in vol % and ppmv)

| Stream Number> (FIG. 4) | 101 | 103 | 107 | 111 | 113 | 301 | 305 | 307 | 309 |
|---|---|---|---|---|---|---|---|---|---|
| Component | | | | | | | | | |
| Nitrogen | | 0.38% | 0.08% | | 0.88% | 78.05% | 97.50% | 1.22% | 1.06% |
| Oxygen | | 99.51% | | | | 20.98% | 1.31% | | |
| Argon | | 0.10% | 0.02% | 19.04% | 0.23% | 0.93% | 1.14% | 0.32% | 0.28% |
| Neon | | | | | | 18.17 ppm | 22.72 ppm | | |
| Helium | | | | | | 5.24 ppm | 6.55 ppm | | |
| Krypton | | 5.69 ppm | 1.24 ppm | 73.87% | 3.81 ppm | 1.14 ppm | | 14.2 ppm | 12.4 ppm |
| Xenon | | 0.45 ppm | 0.10 ppm | 7.09% | 0.04 ppm | 0.09 ppm | | 0.66 ppm | 0.59 ppm |
| Hydrogen | | | 50.08% | | 17.70% | 10.0 ppm | 12.50 ppm | 23.94% | 27.53% |
| Carbon monoxide | | | 26.46% | | 6.33% | 19.99 ppm | 25.00 ppm | 8.61% | 11.06% |
| Carbon dioxide | | 5.00 ppm | 3.48% | | 42.31% | 0.04% | 0.05% | 31.06% | 27.27% |
| Methane | 100.0% | 49.9 ppm | 2.49% | | 26.14% | 10.0 ppm | | 34.08% | 29.75% |
| Methanol | | | 0.71 ppm | | 5.27% | | | 0.71% | 0.61% |
| Water | | | 17.39% | | 1.14% | | | 0.06% | 2.44% |
| Flow, lb mol/hour | 29.91 | 20.03 | 92.24 | 1.05E-4 | 8.72 | 100.0 | 79.97 | 579.27 | 671.51 |
| Temperature, °F. | 100.0 | 85.0 | 219.9 | 127.4 | 127.4 | 85.0 | 85.00 | 100.45 | 335.72 |
| Pressure, psia | 2000 | 2000 | 2000 | 200 | 200 | 14.7 | 14.7 | 2000 | 2000 |

| Stream Number> (FIG. 4) | 313 | 317 | 321 | 323 | 325 | 329 | 306 | 401 | 407 |
|---|---|---|---|---|---|---|---|---|---|
| Component | | | | | | | | | |
| Nitrogen | 1.14% | 1.14% | 3.26 ppm | 1.22% | 1.22% | 1.22% | | 0.01% | 0.19% |
| Oxygen | | | | | | | | | |
| Argon | 0.30% | 0.30% | 1.02 ppm | 0.32% | 0.32% | 0.32% | | 36.0 ppm | 0.05% |
| Krypton | 13.4 ppm | 13.4 ppm | 0.08 ppm | 14.2 ppm | 14.2 ppm | 14.2 ppm | | 0.75 ppm | 9.58 ppm |
| Xenon | 0.63 ppm | 0.63 ppm | 0.03 ppm | 0.66 ppm | 0.66 ppm | 0.66 ppm | | 0.13 ppm | 1.38 ppm |
| Hydrogen | 22.40% | 22.40% | 0.01% | 23.94% | 23.94% | 23.94% | | 0.36% | 4.96% |
| Carbon monoxide | 8.06% | 8.06% | 37.8 ppm | 8.61% | 8.61% | 8.61% | | 0.12% | 1.66% |
| Carbon dioxide | 29.42% | 29.42% | 1.41% | 31.06% | 31.06% | 31.06% | | 5.91% | 65.30% |
| Methane | 31.92% | 31.92% | 0.04% | 34.09% | 34.08% | 34.08% | | 0.73% | 9.91% |
| Methanol | 4.30% | 4.30% | 59.11% | 0.71% | 0.71% | 0.71% | | 55.97% | 14.58% |
| Water | 2.46% | 2.46% | 39.43% | 0.06% | 0.06% | 0.06% | 100.0 | 36.90% | 3.35% |
| Flow, lb mol/hr | 625.85 | 625.85 | 37.85 | 585.13 | 579.28 | 5.85 | 7.01 | 40.72 | 2.86 |
| Temperature, °F. | 572.0 | 100.0 | 200.0 | 99.96 | 99.96 | 99.96 | 640.0 | 99.96 | 200.0 |
| Pressure, psia | 1998 | 1996 | 200 | 1994 | 1994 | 1994 | 2000 | 1994 | 200 |

Thus the present invention offers an alternative method for the recovery of krypton and xenon from air without the potential to form flammable hydrocarbon-oxygen mixtures in the krypton-xenon recovery process. The method can be integrated with processes for the production and conversion of synthesis gas into liquid synthesis products wherein the synthesis gas is produced by partial oxidation of hydrocarbons with oxygen.

What is claimed is:

1. A method for recovering krypton and xenon from air which comprises:
   (a) separating an air feed stream into oxygen-enriched and nitrogen-enriched product streams;
   (b) reacting the oxygen-rich product stream with a hydrocarbon feed in a synthesis gas generation process to yield a synthesis gas stream comprising hydrogen, carbon oxides, krypton, and xenon, which synthesis gas stream contains essentially no oxygen;
   (c) introducing the synthesis gas stream into a synthesis gas conversion process and converting the synthesis gas stream into a liquid synthesis product stream and an unreacted synthesis gas stream;
   (d) recycling a portion of the unreacted synthesis gas stream to the synthesis gas conversion process; and
   (e) separating another portion of the unreacted synthesis gas stream into a purge gas stream and a gas product stream enriched in krypton and xenon.

2. The method of claim 1 wherein the hydrocarbon feed is natural gas.

3. The method of claim 1 wherein the liquid synthesis product comprises methanol.

4. The method of claim 1 wherein the liquid synthesis product comprises paraffinic hydrocarbons.

5. The method of claim 1 which further comprises introducing steam into the synthesis gas generation process.

6. The method of claim 1 wherein the separating of the remaining portion of the unreacted synthesis gas stream into the purge gas stream and the gas product stream enriched in krypton and xenon is effected by one or more process steps selected from the group consisting of catalytic combustion, amine-based absorption, condensation and phase separation, pressure swing adsorption, temperature swing adsorption, and cryogenic distillation.

7. The method of claim 1 which further comprises reducing the pressure of the liquid product stream to yield a two-phase reduced-pressure product stream, and separating the two-phase reduced-pressure product stream into a final liquid synthesis product stream and a gas stream enriched in krypton and xenon.

8. The method of claim 7 which further comprises combining the gas stream enriched in krypton and xenon with another portion of the unreacted synthesis gas stream.

9. The method of claim 1 wherein the purge gas stream comprises at least hydrogen, carbon monoxide, and methane.

10. The method of claim 9 wherein a portion of the purge gas stream is recycled to the synthesis gas generation process.

11. The method of claim 9 wherein a portion of the purge gas stream is recycled to the synthesis gas conversion process.

12. The method of claim 11 wherein another portion of the purge gas stream is recycled to the synthesis gas generation process.

13. A method for recovering krypton and xenon from air which comprises:
   (a) separating an air feed stream into oxygen-enriched and nitrogen-enriched product streams in an air separation process;
   (b) reacting the oxygen-rich product stream with a hydrocarbon feed in a synthesis gas generation process to yield a synthesis gas stream comprising hydrogen, carbon oxides, krypton, and xenon, which synthesis gas stream contains essentially no oxygen;
   (c) introducing the synthesis gas stream into a synthesis gas conversion process and converting the synthesis gas stream into a liquid synthesis product stream and an unreacted synthesis gas stream;
   (d) recycling at least a portion of the unreacted synthesis gas stream to the synthesis gas generation process;
   (e) reducing the pressure of the liquid synthesis product stream to yield a two-phase reduced-pressure product stream, and separating the two-phase reduced-pressure product stream into a final liquid synthesis product stream and a gas stream enriched in krypton and xenon; and
   (f) separating the gas stream enriched in krypton and xenon into a purge gas stream and a gas product stream further enriched in krypton and xenon.

14. The method of claim 13 wherein a portion of the unreacted synthesis gas stream is combined with the gas stream enriched in krypton and xenon prior to (f).

15. The method of claim 13 wherein the hydrocarbon feed is natural gas.

16. The method of claim 13 wherein the liquid synthesis product comprises methanol.

17. The method of claim 13 wherein the liquid synthesis product comprises paraffinic hydrocarbons.

18. The method of claim 13 which further comprises introducing steam into the synthesis gas generation process.

19. The method of claim 13 wherein the separating of the remaining portion of the unreacted synthesis gas stream into the gas product stream enriched in krypton and xenon and the purge gas stream is effected by one or more process steps selected from the group consisting of catalytic combustion, amine-based absorption, condensation and phase separation, pressure swing adsorption, temperature swing adsorption, and cryogenic distillation.

20. The method of claim 13 wherein the purge gas stream comprises at least hydrogen, carbon monoxide, methane, krypton, and xenon.

21. The method of claim 20 wherein a portion of the purge gas stream is recycled to the synthesis gas generation process.

22. The method of claim 20 wherein a portion of the purge gas stream is recycled to the synthesis gas conversion process.

23. The method of claim 22 wherein another portion of the purge gas stream is recycled to the synthesis gas generation process.

24. The method of claim 20 wherein a portion of the purge gas stream is recycled to the air separation process.

* * * * *